United States Patent [19]

Wang

[11] Patent Number: 5,149,823
[45] Date of Patent: * Sep. 22, 1992

[54] SULFONAMIDE SUBSTITUTED SPIRODILACTAMS

[75] Inventor: Pen-Chung Wang, Houston, Tex.

[73] Assignee: Shell Oil Company, Houston, Tex.

[*] Notice: The portion of the term of this patent subsequent to Aug. 6, 2008 has been disclaimed.

[21] Appl. No.: 564,528

[22] Filed: Aug. 9, 1990

[51] Int. Cl.$^5$ ............... C07D 491/00; C07D 279/00; C07D 225/04; C07D 267/02

[52] U.S. Cl. ............................ 548/410; 540/453; 540/488; 540/489; 540/490; 540/500; 540/524; 540/525; 544/6; 546/16; 546/18; 546/19; 546/20; 548/147; 548/216

[58] Field of Search ............... 528/323, 324, 87, 335, 528/350, 352, 337, 340; 544/6; 540/453, 488, 489, 490, 500, 524, 525; 546/16, 18, 19, 20; 548/147, 216, 410

[56] References Cited

U.S. PATENT DOCUMENTS

| | | | |
|---|---|---|---|
| 4,528,359 | 7/1985 | Berman et al. | 528/109 |
| 5,037,948 | 8/1991 | Wang | 528/323 |

OTHER PUBLICATIONS

Pine, "Organic Chemistry" McGraw Hill Fifth Ed. pp. 302-303 (1987).

*Primary Examiner*—John Kight, III
*Assistant Examiner*—T. Mosley

[57] ABSTRACT

A novel class of sulfonamoyl-substituted 1,6-diaza[4.4]-spirodilactams, having a sulfonamoyl substituent on the hydrocarbyl group attached to each spiro ring nitrogen atom, is useful for the preparation of polymers, including polyamides and as latent curing agents for epoxy resins.

12 Claims, No Drawings

SULFONAMIDE SUBSTITUTED SPIRODILACTAMS

FIELD OF THE INVENTION

This invention relates to a novel class of sulfonamide-substituted spirodilactams, having sulfonamide moieties on the hydrocarbyl substituents on the spiro ring nitrogen atoms, and to polymers and polyamides containing the sulfonamides.

BACKGROUND OF THE INVENTION

Sulfonamide compounds are well-known classes of compounds that have a variety of uses, including as latent curing agents for epoxy resins, e.g., as in U.S. Pat. No. 4,528,359.

It would be of advantage to provide a novel class of sulfonamide compounds having a plurality of rings within the molecular structure and have such compounds be used to produce polymers, including polyamides, and as latent curing agents for epoxy resins.

SUMMARY OF THE INVENTION

The present invention relates to a novel class of sulfonamide-aliphatic or aromatic-substituted [4.4] spirodilactams and to polymers of such compounds, including 1,6-diazaspiro[4.4]nonane-2,7-diones, having sulfonamide moieties on the aliphatic or aromatic substituents on each of the ring nitrogen atoms of the spirodilactam ring system.

DESCRIPTION OF THE INVENTION

The novel compounds of the invention are sulfonamide-substituted 1,6-diazaspiro[4.4]-nonane-2,7-dione compounds, having a sulfonamide moiety on hydrocarbyl substituents attached to the spiro ring nitrogen atoms, there being up to about 60 carbon atoms in said compounds.

Accordingly, the invention is directed to a sulfonamide-substituted spirodilactam, comprising a spirodilactam compound having nitrogen atoms in the 1- and 6-positions of the spiro ring system and having a sulfonamide moiety on each hydrocarbyl substituent on each spiro ring nitrogen atom. As generically used herein, "sulfonamide" includes compounds in which the nitrogen atom of the sulfonamide group is substituted by hydrogen or hydrocarbyl groups.

The sulfonamide substituted spirodilactam of the invention includes those of the formula I

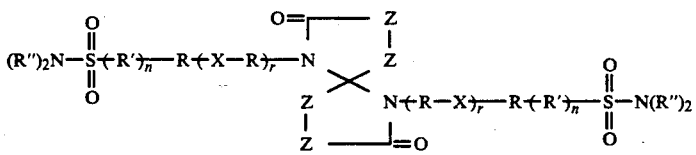

(I)

wherein each R" independently is hydrogen, or an unsubstituted or inertly substituted aliphatic or aromatic group of from 1 to 20 carbon atoms; Z is independently >C(Z') in which Z independently is hydrogen, lower alkyl of up to 4 carbon atoms, preferably methyl, halogen, preferably the lower halogens, fluoro or chloro, or aryl of up to 10 carbon atoms, preferably phenyl, or Z is such that the two adjacent Z groups, taken together form a ring system Z" of 1 to 2 rings, each ring having from 5 to 7 ring atoms, up to two of which are heteroatoms selected from nitrogen atoms, oxygen atoms or sulfur atoms with the remainder of the ring atoms being carbon atoms, there being up to 14 carbon atoms in each Z", two of which ring carbon atoms form a bridge between the two carbon atoms (spiro and carbonyl carbon atoms) connected by the adjacent Z groups. In the above formula I, R independently is an aromatic group of up to 18 carbon atoms which can have up to 4, preferably 2, aromatic rings, inclusive; R' is an aliphatic group of up to 10 carbon atoms, inclusive. Each of R and R' is hydrocarbyl, i.e., contains only atoms of carbon and hydrogen, or is substituted hydrocarbyl containing additional atoms in the form of inert substituents, such as halogen, preferably the middle halogens, chlorine or bromine, haloalkyl, alkyl, alkoxy, alkythio, tertiary-amino, tertiary-aminoalkyl, in which each alkyl group has up to 10 carbon atoms, preferably 4 carbon atoms, or aryloxy of up to 10 carbon atoms and 1 to 2 rings. The terms n and r in the above formula I each independently is 0 or 1 and X is a direct valence bond, or X is alkylene of up to 8 carbon atoms, inclusive, oxy, thio, sulfonyl, carbonyl, dioxyphenylene, i.e.,

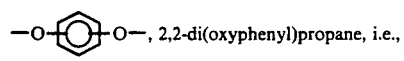, 2,2-di(oxyphenyl)propane, i.e.,

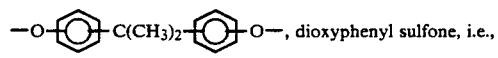, dioxyphenyl sulfone, i.e.,

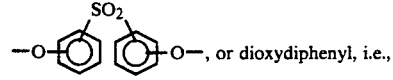, or dioxydiphenyl, i.e.,

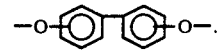.

Each R" preferably is hydrogen or an alkyl group of from 1 to 4 carbon atoms, e.g., methyl or ethyl, an alkenyl or alkynyl group of 2 to 4 carbon atoms, e.g., allyl or propargyl, or an aryl group of up to 10 carbon atoms such as phenyl, phenyethyl or naphthyl.

Sulfonamide-spirodilactams of a considerable variety of structures are included in the compounds of the invention. In the embodiment of the invention wherein R" is H and the moieties of the above compounds of the formula I are not part of a fused ring system and are therefore acyclic, i.e., Z is >C(Z')$_2$, the spirodilactam is illustrated by 1,6-di(4-sulfonamoylphenyl)-1,6-diazaspiro[4.4]nonane-2,7-dione, 1,6-di(3-sulfamoyl-4-chlorophenyl)-3,8-dimethyl-1,6-diazapiro[4.4]nonane-2,7-dione, 1,6-di(3-sulfonamoylphenyl)-3,8-diphenyl-1,6-diazaspiro[4.4]nonane-2,7-dione, 1,6-di-[4-(4-sulfonamoylbenzyl)phenyl]-1,6-diazaspiro[4.4]nonane-2,7-dione, 1,6-di(4-sulfonamoylphenyl)-3,3,4,4,8,8,9,9-octamethyl-1,6-diazaspiro[4.4]-nonane-2,7-dione, 1,6-di[4-(4'-sulfonamoylbiphenyl)]-3,3-dimethyl-1,6-diazaspiro[4.4]nonane-2,7-dione, 1,6-di(4-sulfonamoylmethylphenyl)-1,6-diazaspiro[4.4]nonane-2,7-dione, 1,6-di[2-(4-sulfonamoylphenyl)propyl]1,6-diazaspiro[4.4]nonane-2,7-dione, 1,6-di[4-(4-sulfonamoylphenylisopropyl)phenyl]-1,6-diazaspiro[4.4]-nonane-2,7-dione and the like. In the embodiment wherein R" is hydrogen, and the adjacent Z moieties on each ring form a cyclic structure fused to the spiro ring system, illustrative spirodilactams include 1,6-di(4-sulfonamoylphenyl)-3,4,8,9-dibenzo-1,6-diazaspiro[4.4]-nonane-2,7-dione, 1,6-di(4-sulfonamoylmethylphenyl)-3,4,8,9-dibenzo-1,6-diazaspiro[4.4]nonane-2,7-dione, 1,6-di[4-(4-sulfonamoylphenyl)phenyl]-3,4, 8,9-dipyrido-1,6-diazaspiro[4.4]-nonane-2,7-dione and 1,6-di[4-(4-sulfonamoylphenyloxy)phenyl]-3,4,8,9-di(cyclopentano)-1,6-diazaspiro[4.4]nonane-2,7-dione and the like. Also suitable are those spirodilactams wherein one spiro ring has a fused ring substituent and the other spiro ring is free of fused ring substituents, e.g., 1,6-di(4-sulfonamoylphenyl)-3,4-benzo-8-methyl-1,6-diazaspiro[4.4]nonane-2,7-dione, 1,6-di[1-(4-sulfonamoylnaphthyl)]-3,4-cyclohexano-1,6-diazaspiro[4.4]nonane-2,7-dione and the like.

Of course, the corresponding compounds of formula I, wherein the N-(R")₂ group in which R" is hydrogen in the above-named compounds is replaced by the corresponding group in which one or both of R" is other than hydrogen, e.g., methyl, ethyl, allyl, propargyl, phenyl, phenethyl, 4-styrylmethyl, naphthyl or the like are also illustrative of the compounds of the invention.

In general, compounds of the above formula I wherein R is aromatic and hydrocarbyl are preferred, especially such compounds wherein each n and r is 0. The class of 1,6-di(sulfonamoylphenyl) spirodilactams is particularly preferred. Within the spirodilactam portion of the compounds of formula I spirodilactam rings which are substituted with hydrogen or methyl or fused with benzo rings are generally preferred, particularly the 1,6-diazaspiro[4.4]nonane-2,7-dione compounds.

The sulfonamide-substituted spirodilactams of the above formula I are prepared by reaction of at least one —S(O)₂N(R")₂-containing primary amino compound and a spirodilactam precursor. In terms of the spirodilactam of the above formula I, the —S(O)₂N(R")₂-containing primary amino compound is represented by the formula II

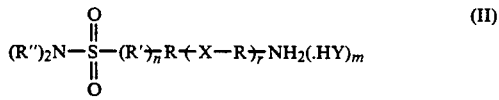

wherein R", R, R', X, n and r have the previously stated meanings; m is 0 or 1; and HY is an acid which forms a salt with the amine, including both inorganic and organic acids which do not interfere with the reaction, such as hydrohalogenic acids, such as hydrochloric and hydrobromic; sulfur acids, such as sulfuric or sulfonic; phosphorus acid, such as phosphoric or phosphonic; and organic acids, such as oxalic acid and the like. Preferably Y is halogen, e.g., fluorine, chlorine, bromine or iodine, but is preferably middle halogen chlorine or bromine. Examples of compounds of formula II include 4-aminobenzenesulfonamide, 4-amino-2-ethylbenzenesulfonamide, 4-amino-2-chlorobenzenesulfonamide, 4-aminobenzenesulfonamide, p-aminophenylsulfonamide, and salt thereof and the like. Such amines are known in the art as, for example, aminobenzenesulfonamides as in U.S. Pat. Nos. 3,889,546 or 4,528,359, the disclosures of which are incorporated herein by reference, or are prepared by known techniques.

The spirodilactam precursor is a 4-oxoheptanedioic acid compound or a 1,6-dioxospiro[4.4]nonane-2,7-dione. In terms of the spirodilactam of the above formula I, the 4-oxoheptanedioic acid compound spirodilactam precursors are represented by the formula III

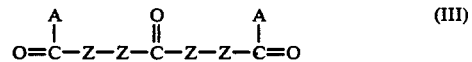

wherein Z has the previously stated meaning and A is hydroxy, lower alkoxy or halo, preferably middle halo.

When the Z moieties are linked together to form a ring system the ring system is aromatic, cycloaliphatic or heterocyclic and is hydrocarbyl containing only atoms of carbon and hydrogen besides any heteroatoms or substituted hydrocarbon containing additional atoms such as halogen, preferably middle halogen, in the form of inert carbon atom substituents.

In one embodiment employing the ketodiacid compound spirodilactam precursor, each Z moiety is >C(Z')₂ and the ketodiacid compound is an 4-oxoheptanedioic acid compound. In one such embodiment, largely because of a particularly convenient method of producing the spirodilactam precursor, a preferred 4-oxoheptanedioic acid compound has at least one hydrogen on the carbon atom adjacent to each carboxy function, that is, at least one Z' on each carbon atom adjacent to a carboxy function is hydrogen. Such 4-oxoheptanedioic acid compounds are represented by the formula IIIa

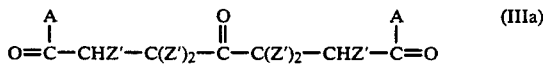

wherein Z' and A have the previously stated meanings. Such 4-oxoheptanedioic acid compounds include 4-oxoheptanedioic acid, dimethyl 4-oxoheptanedioate, 2,6-dimethylheptanedioic acid, 2,3,5,6-tetramethyl-4-oxoheptanedioyl chloride, di-n-propyl 2,6-di-n-butyl-4-heptanedioate, 6-carbomethoxy-3,3,5,5-tetramethyl-4-oxohexanoic acid and the like. The preferred ketodiacids of the above formula IIIa are those wherein each Z' is hydrogen or methyl, especially hydrogen, and each A is hydroxy or methoxy, especially hydroxy.

These ketodiacid compounds are known compounds or are produced by known methods, but the esters of formula IIIa, i.e., the compounds wherein A is alkoxy, are produced by reaction of formaldehyde with an α,β-ethylenically unsaturated carboxylic acid ester such as methyl acrylate, ethyl methacrylate, methyl crotonate, methyl ethacrylate, propyl 2,3-dimethylbutanoate and the like. This reaction is conducted in the presence of a catalyst system which comprises a thiazolium salt and a tertiary amine and produces the dialkyl 4-oxoheptanedioate derivative in good yield. This process is described in greater detail in copending U.S. Pat. No. 4,800,231, incorporated herein by reference. Conversion of the esters thereby obtained to free acids or acid halides is by conventional methods as is the general interconversion of the acids, esters or acid halides of formula IIIa.

In a second embodiment of the ketodiacid compound spirodilactam precursor, the 4-ketodiacid incorporates cyclic moieties between the keto group and the carboxy function, i.e., two adjacent Z moieties form a fused cyclic ring structure Z''. Such diacid compounds are represented by the formula IIIb

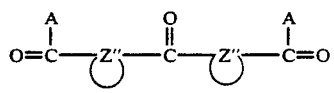 (IIIb)

wherein A and Z'' have the previously stated meanings. Illustrative of these cyclic ketodiacid compounds are di(2-carboxycyclohexyl) ketone, di(2-carboxyphenyl) ketone, di(2-carbopropoxycyclo-4-pentenyl) ketone, di(2-chlorocarbonylphenyl) ketone, di(2-carboxypyridyl) ketone, 2-carboxyphenyl N-methyl-3-carboxy-2-pyrryl ketone, di(3-carbethoxy-2-morpholyl) ketone, di(3-carbomethoxy-2-napthyl) ketone and the like. The preferred cyclic ketodiacid compounds of formula IIIb are those wherein each Z'' is a ring system of from 5 to 6 carbon atoms, inclusive, and up to one nitrogen atom, particularly benzo.

Such ketodiacids are known compounds or are produced by known methods, such as the method of U.S. Pat. No. 1,999,181 or the method of Cava et al, *J. Am. Chem. Soc.*, 77, 6022 (1955).

In yet another embodiment of the diketone compound spirodilactam precursor, the ketodiacid incorporates one fused cyclic moiety with the remainder of the Z moieties being >C(Z')$_2$, i.e., the compounds are of the formula IIIc

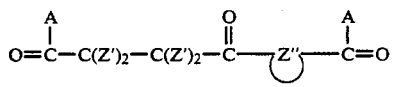 (IIIc)

wherein A, Z' and Z'' have the previously stated meanings. Such ketodiacids of one cyclic moiety are illustrated by 3-(2-carboxybenzoyl)propionic acid, 3-(2-carbomethoxy-2-pyridyloyl)-2-ethylpropionic acid, ethyl 3-(2-carbethoxybenzoyl)propionate, 3-(2-carboxy-4-methylbenzoylbutyrl) chloride and the like. The ketodiacids of the above formula IIIc are known compounds or are produced by known methods. For example, 2-carboxymethylbenzaldehyde reacts with methyl acrylate according to the general teachings of U.S. Pat. No. 4,800,231, to produce methyl 3-(2-carbomethoxybenzoyl)propionate.

In another embodiment of the invention, the spirodilactam precursor is a 1,6-dioxaspiro[4.4]nonane-2,7-dione compound wherein the spiro ring system is substituted with hydrogen, alkyl or halogen, or which incorporates fused cyclic substituents which include the 3- and 4- spiro ring positions and/or the 8- and 9-spiro ring positions of the spiro ring system.

The spirodilactone spirodilactam precursor, in terms of the spirodilactams of formula I, is represented by the formula IV

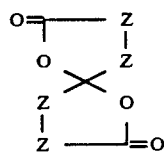 (IV)

wherein Z has the previously stated meaning.

In the embodiment of these spirodilactone spirodilactam precursors of the above formula IV wherein each Z is >C(Z')$_2$, the spirodilactone is represented by the formula IVa

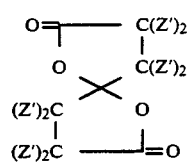 (IVa)

wherein Z' has the previously stated meaning. Illustrative of such spirodilactones are 1,6-dioxaspiro[4.4]nonane-2,7-dione, 3,8-dimethyl-1,6-dioxaspiro[4.4]nonane-2,7-dione, 3,4,8,9-tetramethyl-1,6-dioxaspiro[4.4]nonane-2,7-dione, 4,9-diphenyl-1,6-dioxaspiro[4.4]nonane-2,7-dione, 3,3,8,8-tetramethyl-1,6-dioxaspiro[4.4]nonane-2,7-dione, 3,3,4,4,8,8,9,9-octamethyl-1,6-dioxaspiro[4.4]nonane-2,7-dione, 3,4,8,9-tetrafluoro-1,6-dioxaspiro[4.4]nonane-2,7-dione and the like. The preferred spirodilactones of the above formula IVa are those wherein at least one Z' of each Z'-substituted carbon atom is hydrogen.

The compounds of formula IVa are known compounds or are produced by known methods such as the process of Pariza et al, *Synthetic Communications*, Vol. 13(3), pp. 243–254 (1983), herein incorporated by reference.

In the embodiment of the spirodilactone spirodilactam precursors of the above formula IV which incorporates a fused cyclic moiety as a part of the two rings of the spiro ring system, the spirodilactones are represented by the formula IVb

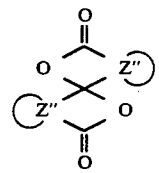 (IVb)

wherein Z'' has the previously stated meaning. Typical compounds of this formula IVb are 3,4,8,9-dibenzo-1,6-dioxaspiro[4.4]nonane-2,7-dione, 3,4,8,9-di(cyclopentano)-1,6-dioxaspiro[4.4]nonane-2,7-dione, 3,4,8,9-di(4-methylbenzo)-1,6-dioxaspiro[4.4]nonane-2,7-dione, 3,4,8,9-di-(pyrido)-1,6-dioxaspiro[4.4]nonane-2,7-dione and the like. These compounds are known compounds or are produced by known methods including the method described by Conover et al., U.S. Pat. No. 1,999,181, Cava et al., *J. Am Chem. Soc.*, 77, 6022 (1955), or Gourmelon et al., *Bull. Soc. Chem.* 4032 (1971). Such methods include (1) in Conover et al., the decarboxylation of dicarboxylic acid anhydrides in the presence of known decarboxylation catalysts, (2) in Cava et al., the chromic acid oxidation of cyclic (aryl) substituted dicyclic (diarylene) compounds, and (3) Gourmelon et al., the Friedel Crafts condensation of cyclic (aryl) acid with cyclic (aryl) dicarboxylic anhydride. Other methods include Cava et al., *J. Am. Chem. Soc.*, 79, 1706 (1957) in which a fused ring-cyclobutene dibromide is treated with potassium hydroxide followed by oxidation with chromic acid in acetic acid, and Sikes et al., *Meeting Am. Chem. Soc.*, April 1988, p. 614, in which a cyclic magnesium bromide having an o-tolyl group is reacted with an excess of a dicarboxylic acid anhydride in benzene-ether solution followed by oxidation with chromium (VI) oxide in glacial acetic acid. Using these methods, spirodilactones substituted at the 3-, 3,5-, 3,4,5- or 3,4,5- and 6-positions can be prepared.

In a third embodiment of the spirodilactone spirodilactam precursor, a cyclic moiety is fused to one spiro ring and the other spiro ring is free from fused ring substituents. Such spirodilactones are represented by the formula IVc

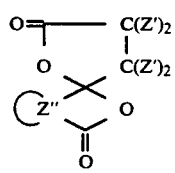
(IVc)

wherein Z' and Z" have the previously stated significance. Such spirodilactones are illustrated by 3-methyl-8,9-benzo-1,6-dioxaspiro[4.4]nonane-2,7-dione, 3,4-benzo-1,6-dioxaspiro[4.4]nonane-2,7-dione, and 3,3,4,4-tetramethyl-8,9-morphoyl-1,6-diazaspiro[4.4]nonane-2,7-dione and the like. The spirodilactones of the above formula IVc are produced by known methods, for example, the dehydration of the corresponding ketodiacid. By way of illustration, 3,4-benzo-1,6-dioxaspiro[4.4]nonane-2,7-dione, is produced by dehydration of 3-(2-carboxybenzoyl)propionic acid through application of heat.

In general, the preferred spirodilactone spirodilactam precursors are hydrocarbon except for the oxygen atoms of the lactone moieties, and particularly preferred are those spirodilactones which are free from fused ring substituents (formula IVa) or those which have a fused ring substituent on each of the spiro rings (formula IVb). An especially preferred spirodilactone spirodilactam precursor of the first class is 1,6-dioxaspiro[4.4]nonane-2,7-dione.

The acyclic 4-oxoheptanedioic acid compounds are known or are produced by the methods described above, but certain of the esters are also produced by the reaction of formaldehyde and unsaturated carboxylic acid esters by the process disclosed and claimed in U.S. Pat. No. 4,800,231. Interconversion of the acids, esters or acid halides of formula III is by conventional methods. The production of 4-oxoheptanedioic acid compounds of formula IV which contain cyclic moieties is by the process of Cava et al, *J. Am. Chem. Soc.*, 77, 6022 (1955). The spirodilactones of formula IIb are produced by the process of Pariza et al, *Synthetic Communications*, Vol. 13(3), pp. 243-254 (1983), or if the spirodilactones have additional fused rings by the process of U.S. Pat. No. 1,999,181.

The $-S(O)_2N(R'')_2$-containing primary amino compound and the spirodilactam precursor react in a molar ratio of 2:1 although in practice reactant ratios from about 8:1 to about 1:1.5 are satisfactory. Reactant ratios of $-S(O)_2N(R'')_2$-containing primary amino compound to spirodilactam precursor which are substantially stoichiometric are preferred. Reaction is conducted in a liquid phase solution in an inert reaction diluent such as an N-alkylamide, e.g., N,N-dimethylformamide, N,N-dimethylacetamide, N-methyl-2-pyrrolidone and the like. Reaction takes place under reaction conditions at an elevated temperature, typically from about 80° C. to about 250° C., and at a reaction pressure sufficient to maintain the reaction mixture in a liquid phase, e.g., pressures up to about 20 atmospheres. Subsequent to reaction the spirodilactam product is recovered from the reaction product mixture by conventional methods such as solvent removal, precipitation and chromatographic separation and the like. Recovery of the spirodilactam product is not required, however, and particularly in cases where substantially stoichiometric quantities of reactants were employed the spirodilactam can be used directly for the various utilities later described.

Sulfonamides of the invention wherein R" is a group having carbon-to-carbon terminal unsaturation, such as allyl, propargyl, 4-styrylmethyl and the like, find utility in cured products, such as surface coatings, adhesives or composites. The curing is accomplished by conventional methods such as thermal or photochemical excitation, by catalyzed polymerization employing cationic or anionic catalysts, or by reaction with a polyfunctional curing agent. Anionic polymerization uses alkali metal alcoholates, hydroxides or amides as catalysts while typical cationic polymerization catalysts are inorganic or organic acids or are Lewis acids. Such cationic catalysts include sulfuric acid, phosphoric acid, p-toluenesulfonic acid, boron-trifluoride and tin tetrachloride. Catalytic catalysts are generally employed in a quantity of from about 0.05% by weight to about 5% by weight, based on total composition.

The invention also includes the use of polyfunctional sulfonamides of the invention, wherein at least one R" in each sulfonamyl substituent is hydrogen, as curing agents for epoxy resins. By "polyfunctional" is meant that there are two or more hydrogen atoms in the sulfonamide substituents and at least one R" in each sulfonamide substituent is hydrogen. In particular, such polyfunctional sulfonamides of the invention are useful as latent curing agents. In such case, the sulfonamides are prereacted with an epoxy compound containing at least one vicinal epoxy group without curing to a thermoset condition, thereby producing a latent, self-curing epoxy resin which is capable of being employed in high solids applications with suitable viscosities at relatively low temperatures. Curing, however, is subsequently accomplished at relatively high temperatures.

One aspect of the present invention pertains to resin compositions resulting from heating, at a temperature which is sufficient to cause a reaction between the epoxy groups and the sulfonamide groups, preferably above about 200° C., most preferably not greater than about 250° C. for a time sufficient to complete the reaction between the sulfonamide groups and the epoxy groups; a composition comprising (A) at least one epoxy resin having an average of more than one 1,2-epoxy groups per molecule and (B) at least one sulfonamide compound of the invention wherein components (A) and (B) are employed in quantities which provide about a stiochiometric amount of sulfonamoyl group, $-S(O)_2NHR$, in the sulfonamide of the invention for each epoxy group in the resin.

Another aspect of the present invention pertains to an article resulting from subjecting a composition containing the aforementioned latent, self-curing composition to a temperature of at least about 150° C., preferably from about 150° C. to about 250° C., most preferably from about 175° C. to about 225° C. for a time sufficient to complete curing thereof.

Suitable polyepoxides used to prepare the present compositions comprise those compounds containing at least one vicinal epoxy or oxirane group, i.e., at least one

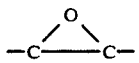

group. These polyepoxides may be saturated or unsaturated, aliphatic, cycloaliphatic, aromatic or heterocyclic and may be substituted if desired with non-interfering substituents such as halogen atoms, hydroxyl groups, ether radicals, and the like. They may also be monomeric or polymeric.

For clarity, many of the polyepoxides and particularly those of the polymeric type are described in terms of epoxy equivalent values. The meaning of this expression is described in U.S. Pat. No. 2,633,458. The polyepoxides used in the present process are preferably those having an epoxy equivalency greater than 1.0.

Various examples of liquid polyepoxides that may be used in the process of the invention are given in U.S. Pat. No. 2,633,458 and it is to be understood that so much of the disclosure of that patent relative to examples of polyepoxides is incorporated by reference into this specification.

Other suitable polyepoxides are disclosed in U.S. Pat. Nos. 3,373,221 and 3,377,406 and the disclosure relevant to examples of epoxy compounds is incorporated by reference into this specification.

Preferred polyepoxides are the glycidyl polyethers of polyhydric phenols and polyhydric alcohols, especially the glycidyl polyethers of 2,2-bis(4-hydroxyphenyl)propane having an average molecular weight between about 300 and 3,000 and an epoxide equivalent weight between about 140 and 2,000.

Other suitable epoxy compounds include those compounds derived from polyhydric phenols and having at least one vicinal epoxy group wherein the carbon-to-carbon bonds within the six-membered ring are saturated. Such epoxy resins may be obtained by at least two well-known techniques, i.e., by the hydrogenation of glycidyl polyethers of polyhydric phenols or by the reaction of hydrogenated polyhydric phenols with epichlorohydrin in the presence of a suitable catalyst such as Lewis acids, i.e., boron trihalides and complexes thereof, and subsequent dehydrochlorination in an alkaline medium.

The cured polymers from the epoxide and sulfonamide of the present invention are used for coatings, castings, moldings, structural or electrical laminates or composites or the like.

Further information about latent, self-curing epoxy resin compositions, methods and curing agents based on sulfonamides or co-curing agents that can be used with the present spirodilactam sulfonamides can be found in U.S. Pat. Nos. 4,528,359 and 3,899,546, the disclosures of which are incorporated herein by reference.

Spirodilactam sulfonamides of the invention in which the amine nitrogen atom in the sulfonamoyl group is substituted by inert hydrocarbyl substituents such as alkyl or aryl can be used to impart hydrolytic or thermal oxidative stability, ultraviolet (UV) stabilizers, ultraviolet (UV) curing agents, plasticizers, or flame retardant additives for compositions, such as polymers.

In preparing polyamides, a sulfonamide-spirodilactam, for example, 1,6-di(4-sulfonamoylphenyl)-1,6-diazaspiro[4.4]nonane-2,7-dione, or the acid salt thereof, is reacted with a dicarboxylic acid or reactive derivative thereof, such as salt, ester, or anhydride, under conventional polymerizing conditions known in the art using conventional conditions for the formation of polyamides, e.g., melt polymerization. In some cases, a polymerization catalyst is used in the formation of the polyamide. The dicarboxy compound can be an aliphatic or aromatic dicarboxy compounds such as adipic acid, isophthalic acid, terephthalic acid or any of the dicarboxy compounds and methods, disclosed in U.S. Pat. No. 4,866,155, the disclosures of which are incorporated herein by reference.

The polyamide products are useful for films, fibers, yarns and the like.

The polyamides comprising (a) moieties derived from a spirodilactam compound, said compound having nitrogen atoms in the 1- and 6-positions of the spiro ring system and having a sulfonamide group on the aliphatic or aromatic substituent on each spiro ring nitrogen atom, alternating with (b) moieties derived from a dicarboxy compound.

For example the invention includes polyamides of the formula V

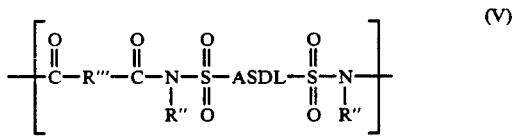

(V)

wherein ASDL is a moiety of an aryl-or alkylaryl-substituted 1,6-diaza [4.4] spirodilactam having aryl or alkylaryl substituents on each spiro nitrogen atom and R''' is an unsubstituted or inertly substituted aliphatic or aromatic group of up to 18 carbon atoms. The group ASDL is represented by formula VI

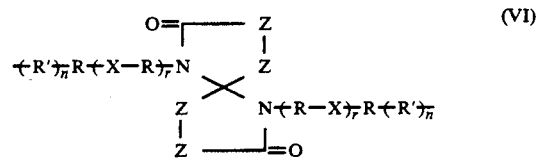

(VI)

In the polyamides R''' is preferably an alkylene group of 2 to 10 carbon atoms or an arylene group of 6 to 10 carbon atoms.

The dicarboxy compound is any conventional diacid or reactive derivative thereof, such as halide, salt, anhydride or the like. Suitable diacids are disclosed in U.S. Pat. No. 4,866,155, the disclosures of which are incorporated herein by reference. Preferably, the diacid is an aromatic acid, such as phthalic acid or the like.

The polyamides are polymers having a molecular weight of from about 1,000 to about 100,000, preferably from about 10,000 to about 50,000.

The invention is further illustrated by the following Illustrative Embodiments which should not be construed as limiting the invention.

ILLUSTRATIVE EMBODIMENT I

A mixture of 34.45 g (0.02 mole) of sulfanilamide, 15.61 g (0.01 mole) of 1,6-dioxaspiro[4.4]nonane-2,7-dione and 75 ml of N-methyl-2-pyrrolidinone (NMP) was placed in a 250 ml round-bottomed flask equipped with a mechanical stirrer and a condenser and warmed with stirring to 170°-180° C. After four days, the mixture was cooled and NMP was removed under reduced pressure. The product was then precipitated in methanol. A $C^{13}$NMR analysis indicated the formation of the desired spirodilactam bis-sulfonamyl product.

ILLUSTRATIVE EMBODIMENT II

A mixture of 4.52 g (0.01 mole) of spirodilactam bis-sulfonamide compound produced by the process of Embodiment I above, 1.66 g (0.01 mole) of terephthalic acid, 0.05 g of tin oxide and 10 ml of diglyme is heated at 170°–180° C. in a nitrogen atmosphere. After the reaction is complete, the reaction mixture is poured into methanol to isolate the polyamide polymer.

ILLUSTRATIVE EMBODIMENT III

A mixture of the spirodilactam bis-sulfonamide of Embodiment 1 above (4.52 g) and bisphenol A diglycidylether (6.60 g) are melted at 150°–180° C. The mixture is then heated in an oven, in a first stage to 200° C. for 2 hours and in a second stage to 220° C. for 2 hours. The resulting product is a hard-cured resin.

What is claimed is:

1. A sulfonamide-substituted spirodilactam compound comprising a spirodilactam compound having nitrogen atoms in the 1- and 6-positions of the spiro ring system and having sulfonamoyl moieties on hydrocarbyl substitutents attached on each spiro ring nitrogen atom, there being up to about 60 carbon atoms in said compound.

2. The compound of claim 1 wherein the derivative is represented by the formula I

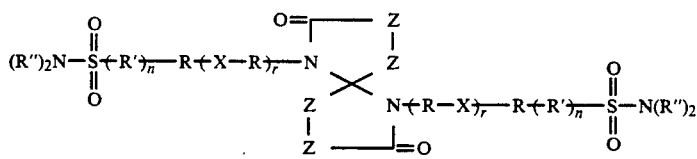

wherein each R" independently is hydrogen, or an unsubstituted or inertly substituted aliphatic or aromatic group of from 1 to 20 carbon atoms; Z independently >C(Z') in which Z' independently is hydrogen, lower alkyl, halogen or aryl of up to 10 carbon atoms or Z is such that the two adjacent Z groups taken together form a ring system Z" of 1 to 2 rings, each ring having from 5 to 7 atoms, up to two of which are heteroatoms selected from nitrogen, oxygen or sulfur, there being up to 14 carbon atoms in each Z", two of which form a bridge between the carbon atoms connected by the adjacent Z groups, R is an aromatic group of up to 18 carbon atoms; R' is an aliphatic group of up to 10 carbon atoms inclusive; n and r each individually is 0 or 1; X is a direct valence bond or X is alkylene of up to 8 carbon atoms inclusive, oxy, thio, sulfonyl, carbonyl, dioxyphenylene, 2,2-di(oxyphenyl)propane or dioxydiphenylene.

3. The compound according to claim 1 wherein each R" is independently hydrogen, an alkyl group of 1 to 4 carbon atoms, an alkenyl or alkynyl group of 2 to 4 carbon atoms or an aryl group of up to 10 carbon atoms.

4. The compound of claim 2 or 3 wherein each n and r is 0.

5. The compound of claim 4 wherein Z is >C(Z')$_2$.

6. The compound of claim 5 wherein Z' hydrogen.

7. The compound of claim 5 wherein R" is hydrogen.

8. The compound of claim 5 wherein R" is alkenyl.

9. The compound of claim 5 wherein R" is alkynyl.

10. The compound of claim 5 wherein R" is aryl.

11. The compound of claim 3 wherein adjacent Z moieties are Z".

12. The compound of claim 11 wherein Z" is benzo.

* * * * *